US00PP11620P

United States Patent [19]

Klemm

[11] Patent Number: Plant 11,620

[45] Date of Patent: Nov. 7, 2000

[54] GERANIUM PLANT NAMED 'KLELENY'

[75] Inventor: Siegfried Klemm, Stuttgart, Germany

[73] Assignee: Klemm + Sohn, Stuttgart, Germany

[21] Appl. No.: 09/250,020

[22] Filed: Feb. 12, 1999

[51] Int. Cl.[7] ..... A01H 5/00

[52] U.S. Cl. ..... Plt./329

[58] Field of Search ..... Plt./329, 325, 328

*Primary Examiner*—Howard J. Locker
*Assistant Examiner*—Wendy A Baker
*Attorney, Agent, or Firm*—C. A. Whealy

[57] ABSTRACT

A new and distinct cultivar of Zonal Geranium plant named 'Kleleny', characterized by its numerous reddish purple-colored flowers with distinct white "eye", upright, compact, uniform and rounded plant habit; freely branching, dense and bushy habit; and dark green leaves.

1 Drawing Sheet

BACKGROUND OF THE INVENTION

The present invention relates to a new and distinct cultivar of Zonal Geranium plant, botanically known as *Pelargonium×hortorum* and hereinafter referred to by the cultivar name Kleleny.

The new Zonal Geranium is a product of a planned breeding program conducted by the Inventor in Stuttgart, Germany. The objective of the breeding program was to develop new cultivars with good cutting production, uniform and freely branching plant habit, and interesting flower colors.

The new Zonal Geranium originated from a cross made by the Inventory of the proprietary *Pelargonium×hortorum* selection identified as Zi 099 as the male, or pollen parent, with the proprietary *Pelargonium×hortorum* selection identified as Zi 105 as the female, or seed parent. The cultivar Kleleny was discovered and selected by the Inventor as a flowering plant within the progeny of the stated cross in a controlled environment in Stuttgart, Germany in 1993 .

Asexual reproduction of the new cultivar by terminal cuttings taken at Stuttgart, Germany, has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'Kleleny'. These characteristics in combination distinguish 'Kleleny' as a new and distinct cultivar:

1. Numerous reddish purple-colored flowers with a distinct white "eye".
2. Upright, compact, uniform and rounded plant habit.
3. Freely branching, dense and bushy growth habit.
4. Dark green leaves.

Compared to the parent selections, the new Zonal Geranium has a more uniform plant habit and a distinct white flower "eye".

Compared to plants of the sibling cultivar, Klelesmo (U.S. Plant patent application Ser. No. 09/250,005 filed concurrently herewith), flowers of plants of the new Zonal Geranium are redder in color and have a more distinct white "eye".

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of 'Kleleny'. Flower and foliage colors in the photograph may appear different from the actual colors due to light reflectance.

DETAILED BOTANICAL DESCRIPTION

The cultivar Kleleny has not been observed under all possible environmental conditions. The phenotype may vary somewhat with variations in environment such as temperature and light intensity, without, however, any variance in genotype. The following observations, measurements and comparisons describe plants grown in Stuttgart, Germany, under commercial greenhouse conditions.

In the following description, color references are made to The Royal Horticultural Society Colour Chart except where general terms of ordinary dictionary significance are used.

Botanical classification: *Pelargonium×hortorum* cultivar Kleleny.

Parentage:

- *Male parent.*—Proprietary *Pelargonium×hortorum* selection Zi 099, not patented.
- *Female parent.*—Proprietary *Pelargonium×hortorum* selection Zi 105, not patented.

Propagation:

- *Type cutting.*—Terminal cuttings.
- *Time to develop roots.*—About 18 to 20 days.
- *Rooting habit.*—Fibrous and freely branching.

Plant description:

- *General appearance.*—Upright, uniform and rounded; compact; vigorous; freely flowering.
- *Crop time.*—About 85 days are required to produce a finished flowering plant from a rooted cutting.
- *Growth and branching habit.*—Rapid growth rate; vigorous; freely branching with about four to five stalks with about two to three stems each. Removal of terminal apices (pinching) is usually not required.
- *Plant height.*—About 15 to 18 cm.
- *Stem length.*—About 7 to 11 cm.
- *Internode length.*—About 1.5 to 2 cm.
- *Foliage description.*—Leaves simple, generally symmetrical, abundant, opposite, smooth. Shape: Mostly rounded with weakly crenated margin. Color: Fully expanded foliage, upper surface: 137A. Fully expanded foliage, lower surface: 137D. Zonation: 176B with 148A; occasionally faint. Petiole length: About 4 to 6 cm.

Flower description:

*Flower type and habit.*—Reddish purple-colored flowers with distinct white "eye". Very freely and continuously flowering. Flowers arranged in umbels arising from apical leaf axils. Umbels initially hemispherical, becoming spherical in shape. Umbels displayed above or beyond the foliage. Flowers semi-double. Umbels persistent.

*Flowering season.*—Year-round under greenhouse conditions. In the garden, flowering is continuous from spring through summer.

*Quantity of inflorescences.*—Typically about 2 to 3 umbels per lateral stem with about 85 to 95 umbels per plant forming during the flowering season.

*Lasting quality.*—Flowers last about 14 days on the plant and about 3 days as cut flowers.

*Fragrance.*—None.

*Umbels.*—Diameter: About 10 cm. Height: About 10 cm.

*Flowers.*—Quantity per umbel: About 25 to 30. Diameter: About 6 cm. Shape: Cup-shaped.

*Flower buds.*—Length: About 2 cm. Diamter: About 1.2 cm. Shape: Ovoid.

*Petals/petaloids.*—Quantity: About 5 to 7 petals and about 2 to 4 petaloids. Arrangement: Imbricate. Shape: Broad with rounded apex and entire margin. Texture: Soft, satiny. Color: Fully opened, upper surface: 66B; with white eye. Fully opened, lower surface: 72B; with white eye. Petaloids: 72B.

*Sepals.*—Quantity: About five. Shape: Elongated, pointed. Angle: Upright. Color: Outer surface: 147A. Inside surface: 147B.

*Peduncle* (*umbel stem*).—Length: About 2 cm. Strength: Moderate. Angle: Mostly upright. Color: Brownish purple to green.

*Reproductive organs.*—Androecium: Stamens: Typically five or six. Anther size: About 1.5 to 2 mm. Anther color: Orange. Filament length: About 5 to 6 mm. Filament color: White. Pollen color: Orange. Gynoecium: Pistils: Typically one with four or five branches. Style length: About 5 to 6 mm. Style color: Green. Stigma color: Purple.

*Seed.*—Length: about 3 to 4.5 mm. Color: Brown.

Disease resistance: Under commercial conditions, resistance to pathogens common to Zonal Geraniums has not been observed.

Weather tolerance: Flowers of plants of the new Zonal Geranium have been observed to be tolerant to wet and hot conditions.

It is claimed:

1. A new and distinct cultivar of Zonal Geranium plant named 'Kleleny', as illustrated and described.

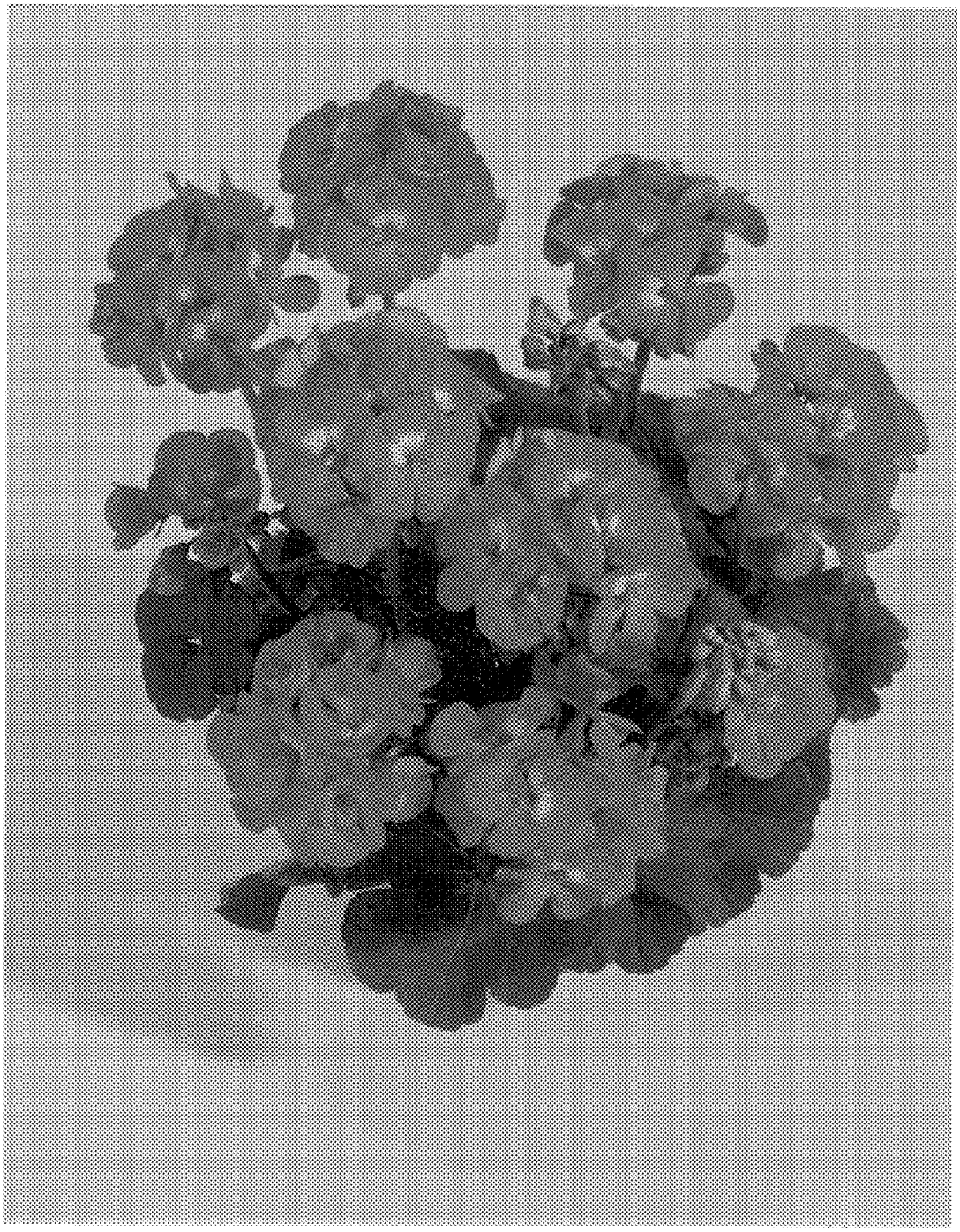

* * * * *